United States Patent [19]
McCarthy et al.

[11] Patent Number: 5,846,245
[45] Date of Patent: Dec. 8, 1998

[54] BONE-ADJUSTING DEVICE

[75] Inventors: Joseph F. McCarthy, Englewood; John S. Crombie, East Hanover, both of N.J.

[73] Assignees: New York University; Howmedica, Inc., both of New York, N.Y.

[21] Appl. No.: 546,208

[22] Filed: Oct. 20, 1995

[51] Int. Cl.$^6$ ................................................. A61B 17/58
[52] U.S. Cl. .............................. 606/105; 606/54; 606/57; 606/59
[58] Field of Search ................................. 606/54–59, 105

[56] References Cited

U.S. PATENT DOCUMENTS

| | | |
|---|---|---|
| 2,346,346 | 4/1944 | Anderson . |
| 2,391,537 | 12/1945 | Anderson . |
| 2,406,987 | 9/1946 | Anderson . |
| 3,849,805 | 11/1974 | Leake et al. ..................................... 3/1 |
| 3,961,854 | 6/1976 | Jaquet ........................................ 403/59 |
| 5,147,358 | 9/1992 | Remmler .................................... 606/57 |
| 5,160,335 | 11/1992 | Wagenknecht ............................ 606/59 |
| 5,184,955 | 2/1993 | Baer et al. ............................... 433/215 |
| 5,376,091 | 12/1994 | Hotchkiss et al. ......................... 606/55 |
| 5,454,810 | 10/1995 | Pohl et al. ................................. 606/59 |

FOREIGN PATENT DOCUMENTS

| | | |
|---|---|---|
| 0 248 138 A1 | 12/1987 | European Pat. Off. . |
| 2 697 994 | 11/1992 | France . |
| 195 03 609 A1 | 8/1995 | Germany . |

OTHER PUBLICATIONS

McCarthy et. al. "Lengthening the Human Mandible by Gradual Distraction", Plastic and Reconstructive Surgery, Jan. 1992, pp. 1–10.

Annino et al., "Distraction Osteogenesis for Reconstruction of Mandibular Symphyseal Defects", AMA Journal, 1994.

Normed Product Advertisement.

*Primary Examiner*—Michael Buiz
*Assistant Examiner*—Daphna Shai
*Attorney, Agent, or Firm*—Pennie & Edmonds LLP

[57] ABSTRACT

A method of performing angular distraction osteogenesis by drilling bone-pin holes into the first and second sides of a segmented bone, inserting bone-pins into the bone-pin holes, attaching the bone-pins in each side of the segmented bone to a distraction device and adjusting the distraction devise so that the bone portion of the first side of the segmented bone angularly adjusts, rotates or pivots its position relative to the bone portion on the second side of the segmented bone in precise, gradual and predetermined incremental amounts over a period of time so that the bone tissue remains healthy and the blood vessels and nerve endings remain intact during the bending distraction process. A device for achieving angular distraction osteogenesis is provided having a support member extending across a segmented piece of bone, members for securing the first side of the segmented bone to the support member and the second side of the segmented bone to the support member, and a member for angularly adjusting the first section of segmented bone relative to the second section of segmented bone. The angular adjustment member includes a gear and a cooperating adjustment screw which rotates the gear when the screw is adjusted in order to easily angularly adjust or rotate the support member or the members for securing the segmented bone pieces to the support member in precise, small incremental predetermined amounts over a period of time. The members for securing the segmented bone pieces to the support member include bone-pin clamps which can be adjusted linearly or translated in precise, gradual and incremental distances along the length of the support member. In one embodiment, the device has two arms, a central joint for angularly adjusting the two arms and two bone-pin clamps for attaching at least one bone-pin on each side of the segmented bone to a respective arm. The arms are attached to the central joint and angularly adjust or rotate in planes that are oriented different from one another and perhaps perpendicularly and the bone-pin clamps linearly translate along each arm.

70 Claims, 11 Drawing Sheets

BONE-ADJUSTING DEVICE

BACKGROUND

The present invention relates generally to a bone-adjusting device which can be used to achieve distraction osteogenesis of bone, particularly as used in humans.

The process of distraction osteogenesis has been employed by orthopedic surgeons to reconstruct and lengthen long bones in the lower extremities. This process involves placing a vascularized piece of bone under tension, thereby inducing native bone formation via the creation of a bony reparative callus which is then placed under tension and generates new bone. ["Distraction Osteogenesis for Reconstruction of Mandibular Symphyseal Defects" by Annino et al.] In order to effect distraction osteogenesis, a surgeon generally performs an osteotomy thereby sectioning or segmenting the bone to be altered into more than one piece and as the bone heals, it is slowly and gradually expanded over a period of time so that the blood vessels and nerve ends remain intact during the distraction process. For instance, the bone may be extended a millimeter a day, often by performing two extensions of half a millimeter, for three or four weeks. Often these distractions are performed by adjustments made by the patient's parent or other close relative or friend.

A device sold by Normed is known which can be used to perform linear distraction. This device is composed of two arms, a central assembly which retains bone-pins and two bone-pin clamps which can be adjusted linearly along the length of the two arms and which also retain bone-pins. The housing assembly allows the angular relation between the arms to be reset or reconfigured in a single plane for the particular patient before the device is fixed to the bone-pins. Once the angular configuration of the arms of the device is set for the patient and fixed to the bone-pins, the angular relation between the arms is fixed and the bone-pin clamps are adjusted along the length of the device to effect linear distraction. This device, although allowing for linear distractions, does not allow continuous infinite angular adjustments in order to achieve angular distraction osteogenesis.

A device as described in U.S. Pat. No. 5,160,335 is known which can be used to perform distraction osteogenesis. This device is a pin-holder support which comprises a clamp for gripping the bone-pins, a jaw which positions the device along a fixation bar, a deflection member for adjusting the angular position of the clamp relative to the fixation bar and a blocking means to maintain the device in a desired position. This device only contemplates distraction along a single axis and does not provide for angular distraction.

A device as described in U.S. Pat. No. 3,961,854 is known which can be used to orient and maintain a rod or stem in any direction. It is composed of a U-shaped element on the branches of which a flange closing the U is detachably secured, at least two cylindrical superposed plates, one of which is rotatably engaged in the flange and the other in the U-shaped element, the adjacent surfaces of the plates each having grooves which cooperatively define a hole to receive the rod or stem to be oriented. This device contemplates distraction along a single axis, and it does not provide for angular distraction.

There are obvious problems with these known prior art devices. These devices provide for linear adjustment only and do not provide for gradual, precise and controlled angular adjustment in order to form curved, bent or other intricately-shaped bones through angular distraction osteogenesis. The importance of being able to form curved sections or portions of bone is demonstrated by angular distraction of the mandible which rounds out the patient's bite and properly contours the face. Moreover, these prior devices do not allow three-dimensional distraction osteogenesis wherein both linear and angular adjustments may be made, both independently or simultaneously, along each of two independent axes defining two different planes.

SUMMARY OF INVENTION

An object of the present invention is to provide a bone-altering device which allows for angular distraction, and in particular, precise, gradual, and easily controlled angular distraction in order to achieve angular distraction osteogenesis so as to form a curved or bent segment of bone. It is a further object to provide a device which can distract both linearly and angularly, both independently and/or simultaneously. It is a further object to provide a device which can distract both linearly and angularly, wherein both the linear and angular distractions can be performed about two independent arms, both independently or simultaneously. It is a further object to provide a device for performing three-dimensional distraction osteogenesis.

A further object of the present invention is to provide a bone-altering device which allows gradual, precise and controlled adjustments to be made easily such as by the patient, parent or other person with no, or relatively little, medical training. It is a further object of the present invention to provide a small, lightweight device which is easily manufactured.

It is still a further object of the invention to provide modular bone-pin clamps which accept varying numbers of bone-pins of the same or different size, for example, two 2 mm or one 3 mm. It is a further object that the bone-pin clamps allow placing the bone-pins as closely as possible, for example less than 10 mm apart, and hold the bone-pins in line with and near the distraction axis. It is a further object to provide a device which allows gradual, incremental linear adjustments independently along two different axes, the linear movement being indexed and calibrated and allowing approximately 20 mm of expansion along each axis.

It is a further object to provide a device which allows gradual, incremental and easily-operated angular changes of the arm(s) which are self-locking to prevent undesired angular movement or rotation. It is still a further object to provide a device with independently activated angularly adjustable or rotatable arms having the centers of rotation of each arm close to the axis of the arm(s) and close to each other. It is a further object to provide an external device and which can be used both for the left and right sides of the patient.

A method of performing angular distraction osteogenesis by drilling bone-pin holes into the first and second sides of a segmented bone, inserting bone-pins into the bone-pin holes, attaching the bone-pins in each side of the segmented bone to a distraction device and adjusting the distraction device so that the first side of the segmented bone angularly adjusts, rotates or pivots its position relative to the second side of the segmented bone in precise, gradual and predetermined incremental amounts over a period of time so that the bone tissue remains healthy and the blood vessels and nerve endings remain intact during the bending distraction process.

The device according to the present invention alleviates the shortcomings of the prior art devices and achieves the aforementioned objects and is used for achieving angular distraction osteogenesis. The device includes a support member which extends across a segmented piece of bone and a means for securing the first side of the segmented bone to the support member and a second side of the segmented bone to the support member and means to angularly adjust, rotate or pivot the first side of the segmented bone relative to the second side of the segmented bone. The device of the present invention allows precise, gradual, incremental and controlled angular adjustments, rotation or pivoting of the bone segments to be made easily over a period of time by a person with no, or relatively little medical training. The segmented pieces of bone are secured to the device by bone-pins which extend out of each side of the segmented bone and are attached to the support member by bone-pin clamps.

The means to angularly adjust the first and second sides of the segmented bone relative to each other may be accomplished by angularly adjusting the bone-pin clamp or the support member and includes having a gear driven by an adjustment screw. The screw cooperates with the gear to angularly adjust or rotate the support member or bone-pin clamp or a portion thereof when the screw is adjusted. The angular adjustment mechanisms are self-locking to prevent any undesired angular movement.

The device according to the present invention also may include bone-pin clamps which adjust linearly along the length of the support member (arm). This linear adjustment may be indexed such as by a ball or protrusion engaging a depression or indentation and/or calibrated with a measurement scale. The bone-pin clamps further may include a locking mechanism to prevent undesired linear translation or movement along the support members (or arms) and may be configured to place the bone-pins in line with and near the bone distraction axis. The device of the present invention further may be provided with a means to retain the bone-pin clamp(s) on the support member (arm).

The device according to the present invention in a different embodiment has two elongated support members, i.e., arms, a means for angularly adjusting these two arms, i.e., a central joint and a means for attaching at least one bone-pin to each of these two arms, i.e., bone-pin clamps. Each arm can be adjusted angularly such that the free end of each arm rotates in a plane around the fixed end of that arm. These respective planes of angular adjustment are different from one another, and may be perpendicular to each other.

The device according to the present invention further may include two separate mechanisms to adjust the angular changes or rotation of the arms, one for each respective arm, and further may be provided with arm-adjustment mechanisms which are self-locking in order to prevent undesired angular movement.

Precise three-dimensional distraction osteogenesis can be performed via independent adjustments in the length and angle of distraction with the device of the present invention. Distraction osteogenesis of the human mandible is one example where three-dimensional adjustability would be helpful. Specifically, this invention allows for linear distraction to occur concurrently along two independent axes. For example, when used to achieve distraction osteogenesis of the mandible, this invention can effect linear expansion independently along the body of the mandible and the ramus. This invention also allows for angular distraction to occur concurrently along two independent axes. Angular distraction of the mandible allows the physician to round out the patient's bite and properly contour the jaw line.

DETAILED DESCRIPTION

Figure 1:
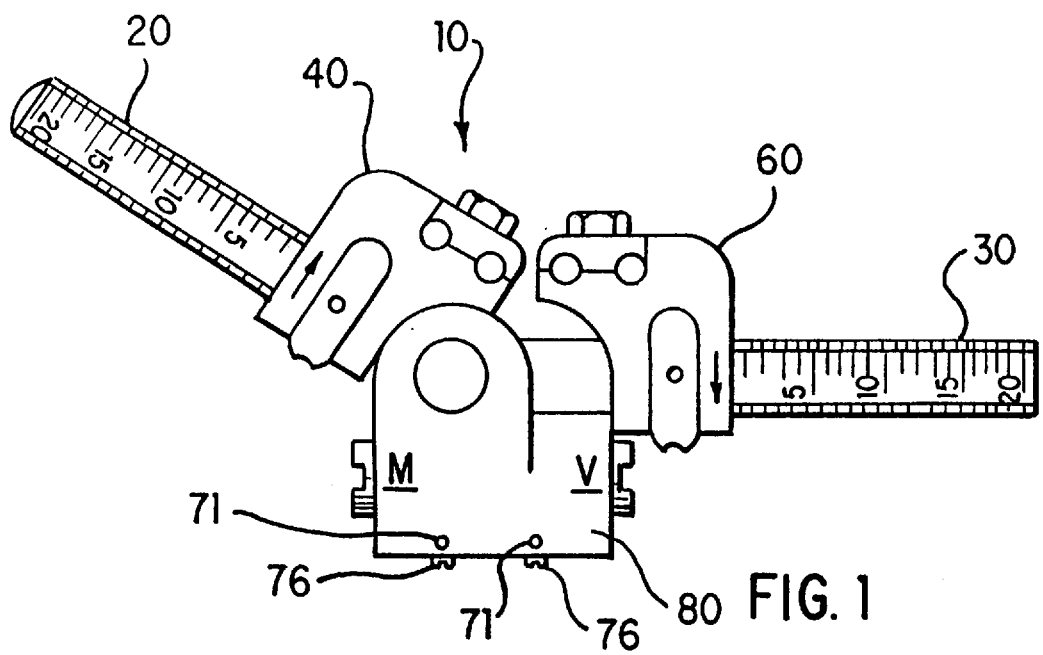
FIG. 1 is a side elevational view of an external bone-lengthening device according to the present invention.
Figure 3:
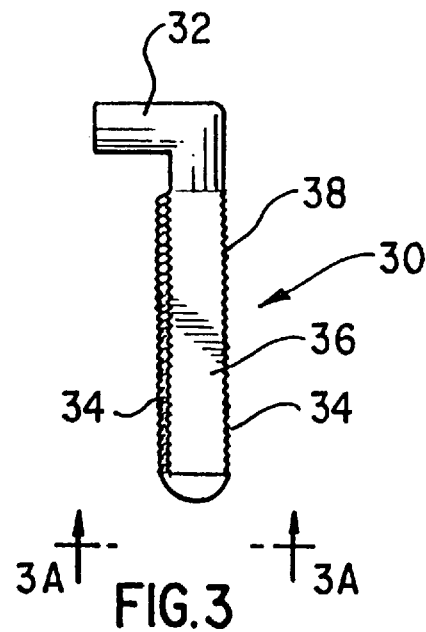
FIG. 3 is a perspective view of the right arm of FIG. 1.

Referring more particularly to the drawings, FIG. 1 shows device 10 which is a preferred embodiment of the present invention and may be used for three-dimensional distraction osteogenesis having a left arm 20, a right arm 30, a central joint 80, a left bone-pin clamp 40 and a right bone-pin clamp 60.

Figure 2:
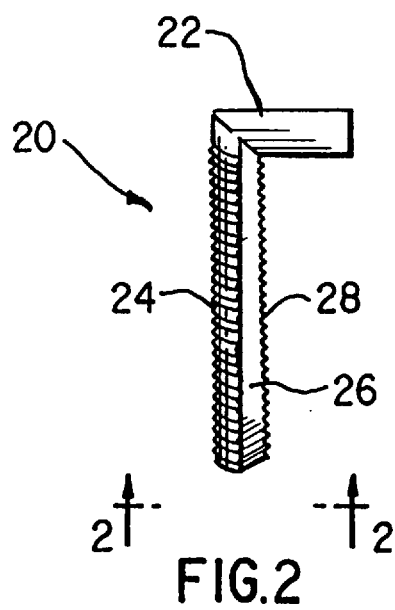
FIG. 2 is a perspective view of the left arm of FIG. 1.
Figure 2A:
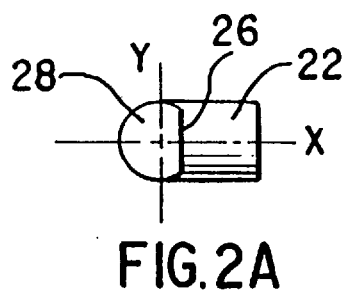
FIG. 2A is an end elevational view of the left arm of FIG. 2.
Figure 3A:
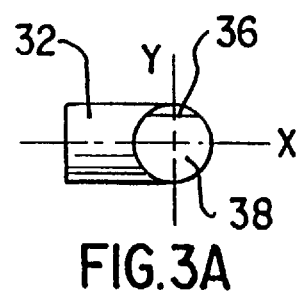
FIG. 3A is an end elevational view of the right arm of FIG. 3.

FIGS. 2, 2A and FIGS. 3, 3A show the left arm 20 and the right arm 30, respectively. Arms 20, 30 are L-shaped, each arm having a head segment 22, 32 which is perpendicular to shaft 28, 38. Each shaft 28, 38 is D-shaped in cross-section and has threaded segments 24, 34 along its partially cylindrical surface and a flat-keyed segment 26, 36, both extending the length of the shaft 28, 38. The arms 20, 30 are substantially identical except for the orientation of flat-keyed segments 26, 36 with respect to head segments 22, 32. Whereas, the flat-keyed segment 26 faces the same direction as the head segment 22 of the left arm 20 as shown in FIG. 2A, the flat-keyed-segment 36 faces 90° clockwise from the head segment 32 of the right arm 30 as shown in FIG. 3A.

Figure 4:
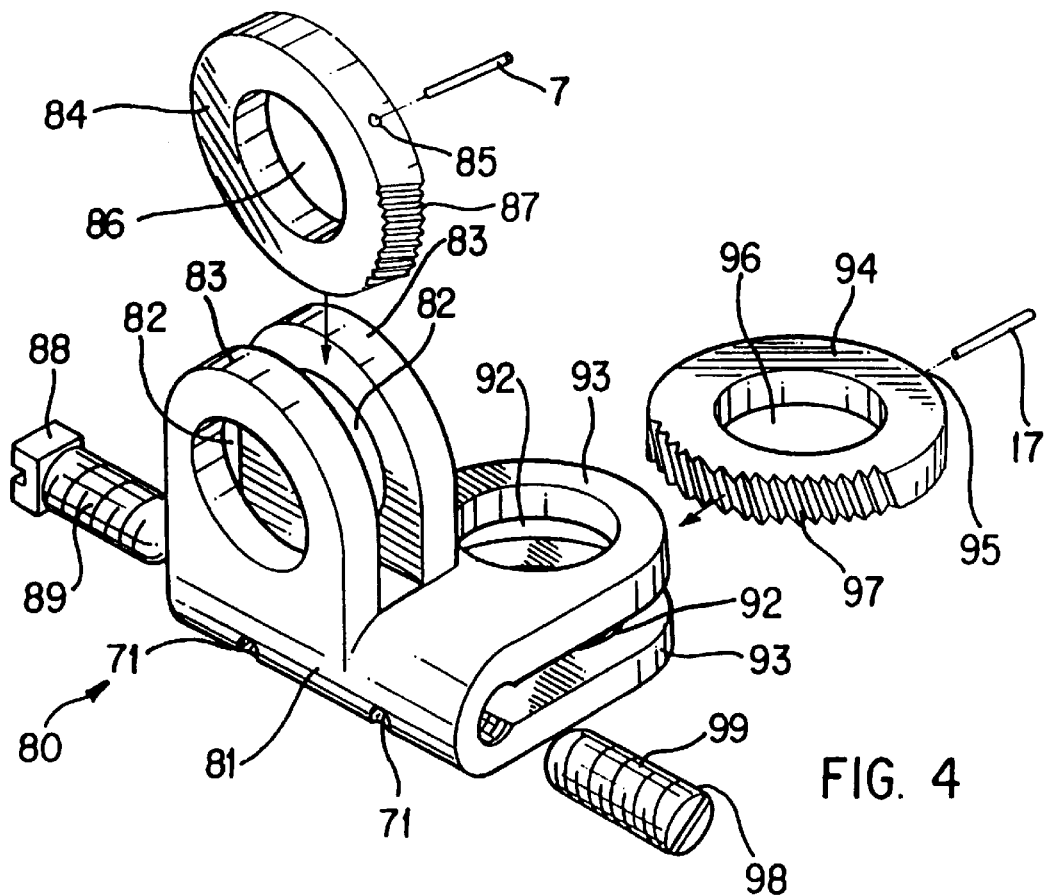
FIG. 4 is a perspective view of the central joint of FIG. 1 with various parts removed in order to show detail.

The central joint 80 as shown in FIG. 4 has a housing 81, two gears 84, 94, and two angular-adjustment screws 88, 98.

The central joint 80 adjusts the angular relation between the arms 20, 30. Housing 81 has two U-shaped supports 83, 93 having respective sets of paired holes 82, 92 which receive and support respective head segments 22, 32 of the arms 20, 30. The U-shaped supports define axes of rotation for the arms 20, 30 and are oriented such that the axes of rotation define differently oriented planes, and preferably, are in perpendicular relation to one another.

Figure 5:
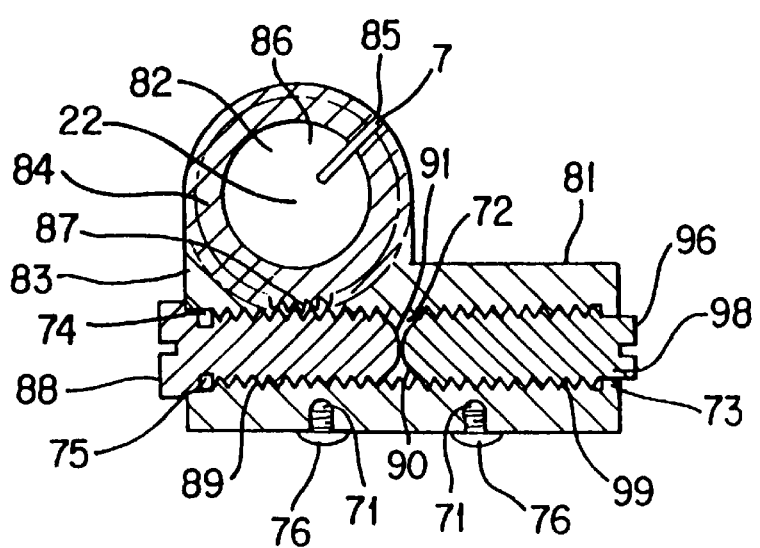
FIG. 5 is a cross-sectional view of an assembled central joint of FIG. 1.

The angular-adjustment screws 88, 98 have threads 89, 99 and are housed within the housing member 81 adjacent to the respective gears 84, 94 as shown in the cross-sectional view of the central joint 80 in FIG. 5. The screw 98 fits within the bore 72 of the housing member 81. The head 96 of screw 98 is the same size as the minimum screw diameter such that the peaks of the threads 99 are of larger diameter than the head 96 of the screw 98. Axial movement of the screw 98 is restricted by threads 99 being retained by the lip 73 of the housing 81 and by the other screw 88 which also fits within the larger bore 72 of the housing member 81. The screw 88 has a circumferential groove 74 which is fitted with pin 75 to restrict axial movement of the screw 88 yet allowing for unrestricted rotational movement.

Each gear 84, 94 has an arm hole 86, 96 and a toothed segment 87, 97 along at least part of its circumference. FIG. 5 shows the central joint with the gear 84 fitted between the U-shaped supports 83 such that the arm hole 86 of gear 84 is aligned with the paired holes 82 of the U-shaped supports 83. In a similar fashion, gear 94 is fitted between U-shaped supports 93 such that arm hole 96 of gear 94 is aligned with paired holes 92 of the U-shaped support 93.

The toothed segments 87, 97 of the gears 84, 94 mesh with the threads 89, 99 of the angular-adjustment screws 88, 98 both to retain angular-adjustment screws 88, 98 within the housing 81 and so that the angular-adjustment screws 88, 98 turn the gears 84, 94. In the preferred embodiment of FIGS. 4 and 5, the housing 81 is configured such that the angular-adjustment screws 88, 98 lie along the same axis such that both may be adjusted easily while the device is in use. In this embodiment, with the screws aligned back-to-back, the ends of the angular-adjustment screws 88, 98 have radii 90, 91 on their ends so that rotational motion is not transferred between them.

Figure 6:
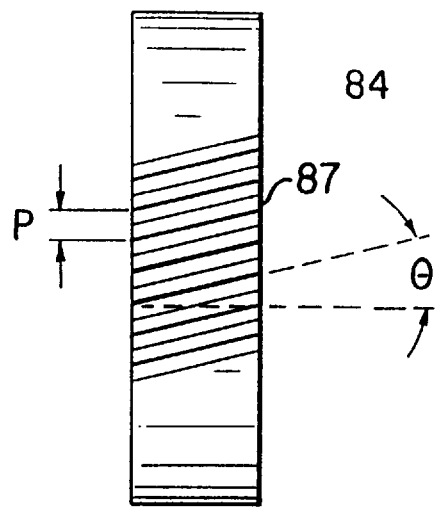
FIG. 6 is an end elevational view of the gear of FIG. 5.

In the preferred embodiment, the angular-adjustment screws 88, 98 have standard machine threads 89, 99 and the toothed segments 87, 97 of the gears 84, 94 have "V-shaped" grooves or teeth which have the same helix angle and pitch as the respective angular-adjustment screws 88, 98. In particular, the helix angle θ which is the angle in which the teeth are formed in the gear with respect to an axis parallel with its axis of rotation as shown in FIG. 6 and the pitch p would be equal to the helix angle and pitch of the machine threads 89, 99 of the angular-adjustment screws 88, 98. In addition, the profile of the "V-shaped" teeth would mate with the machine thread profile to insure proper alignment as the angular-adjustment screws 88, 98 are turned and rotate the respective gears 84, 94.

Alternatively, the gears 84, 94 may be standard gears with involute-shaped teeth such as are well-known in the art, in which case angular-adjustment screws 88, 98 would be standard worm screws configured so as to mate with the teeth of the standard gears. The "V-shaped" teeth are preferred because they require less intricate machining to form the gears and mating worm screws and, in addition, the standard gears would have to be larger than the "V-shaped" teeth gears, but then they would not be able to perform the same precise, gradual and controlled angular-adjustments to the arms of the device.

The head segments 22, 32 of the arms 20, 30 fit through the respective paired holes 82, 92 of the central joint 80 and arm holes 86, 96 of gears 84, 94. Each respective arm 20, 30 is properly oriented and then secured to the gears 84, 94 by any of a number of ways. In this embodiment, pin-holes 85, 95 are drilled into gears 84, 94 and head segments 22, 32 of arms 20, 30 and pins 7, 17 are inserted therein.

In operation, the angular-adjustment screw 88 turns the gear 84 which ultimately pivots or rotates the arm 20 in a plane. Likewise, the angular-adjustment screw 98 turns the gear 94 which ultimately pivots or rotates the arm 30 in a plane. The plane in which the arm 20 rotates is differently oriented from, and in this embodiment, is perpendicular to, the plane in which the arm 30 rotates. The configuration of the central joint 80 as shown in FIG. 4 allows the two independent centers of rotation of the arms 20, 30 to be located in close proximity to each other and within the central portion of the device.

Figure 7:
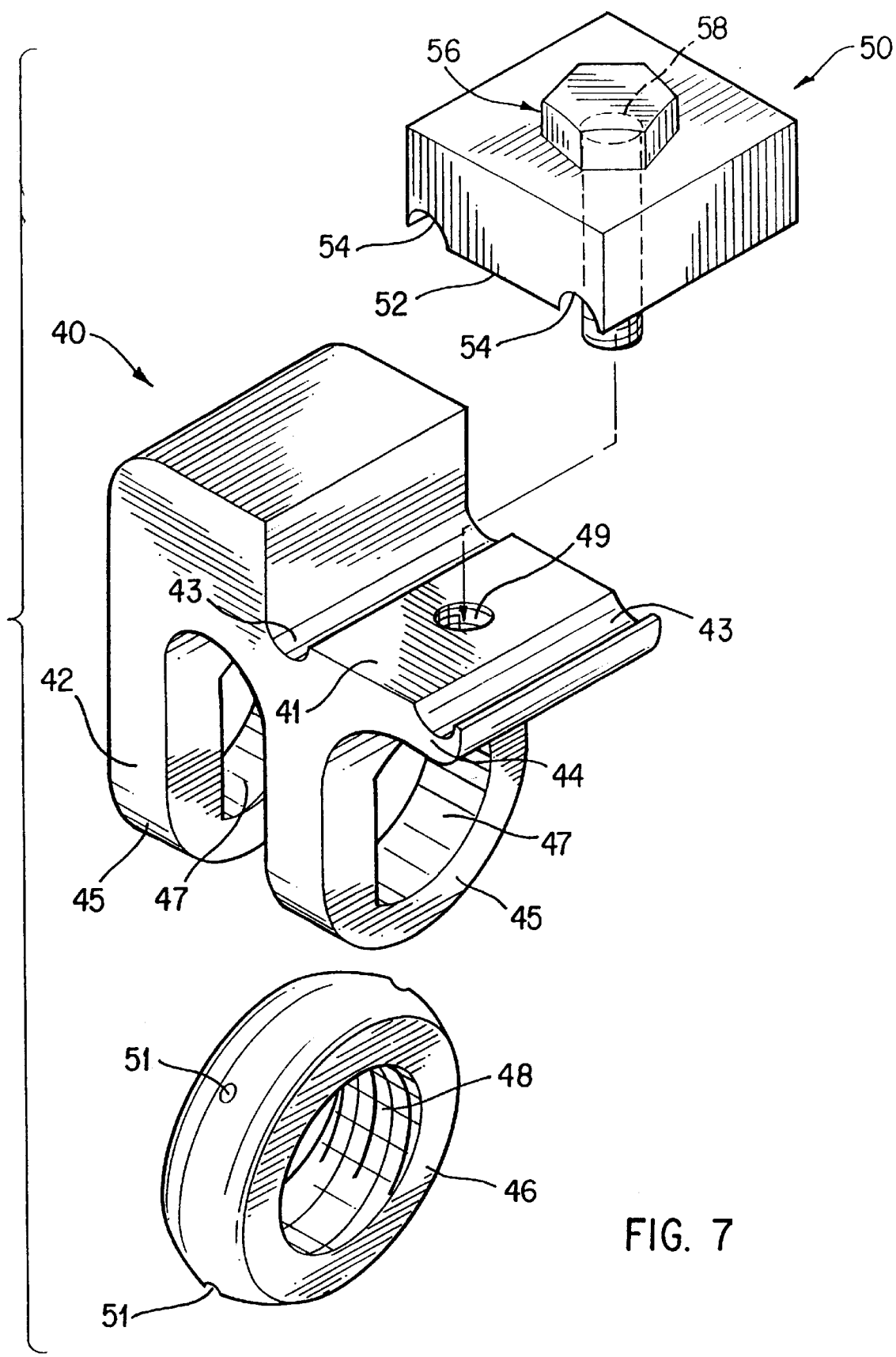
FIG. 7 is a perspective view of the left bone-pin clamp of FIG. 1 with portions broken away to show detail.
Figure 9:
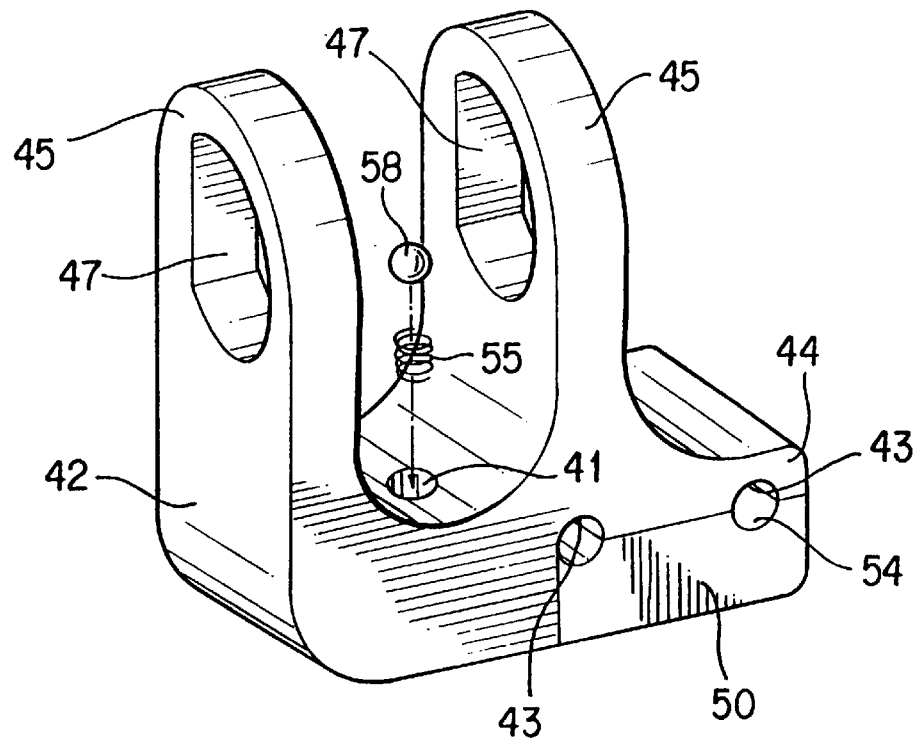
FIG. 9 is a perspective view of the right bone-pin clamp of FIG. 1 with a portion broken away to show detail.

FIG. 7 shows the left bone-pin clamp 40 which has a rider 42, a cap 50, a screw 56 and a wheel 46. The left bone-pin clamp 40 fits around and rides along left arm 20. The rider 42 has two cylindrical extensions 45, a bore 48 (which cannot be seen in FIG. 7, but which is shown in FIG. 9 shown in FIG. 9), an extended portion 44 having a recessed surface 41 extending the width of the rider 42, a screw-hole 49 piercing the recessed surface 41 and two diametrical grooves 43 of a semi-cylindrical shape spaced in parallel extending the entire width of the recessed surface 41.

The two cylindrical extensions 45 have D-shaped bores 47 which are configured to fit around the left arm 20. The D-shaped bores 47 are oriented in the cylindrical extensions 45 such that the bone-pins held by the left bone-pin clamp 40 will remain perpendicular to the face of the flat-keyed segment 26 of the left arm 20 as the left bone-pin clamp 40 rides along the left arm 20. In addition, the D-shaped bores 47 are oriented in the cylindrical extensions 45 such that the extended portion 44 of the rider 42 is directed toward the central joint 80 when the left bone-pin clamp 40 is assembled onto the left arm 20.

Figure 8:
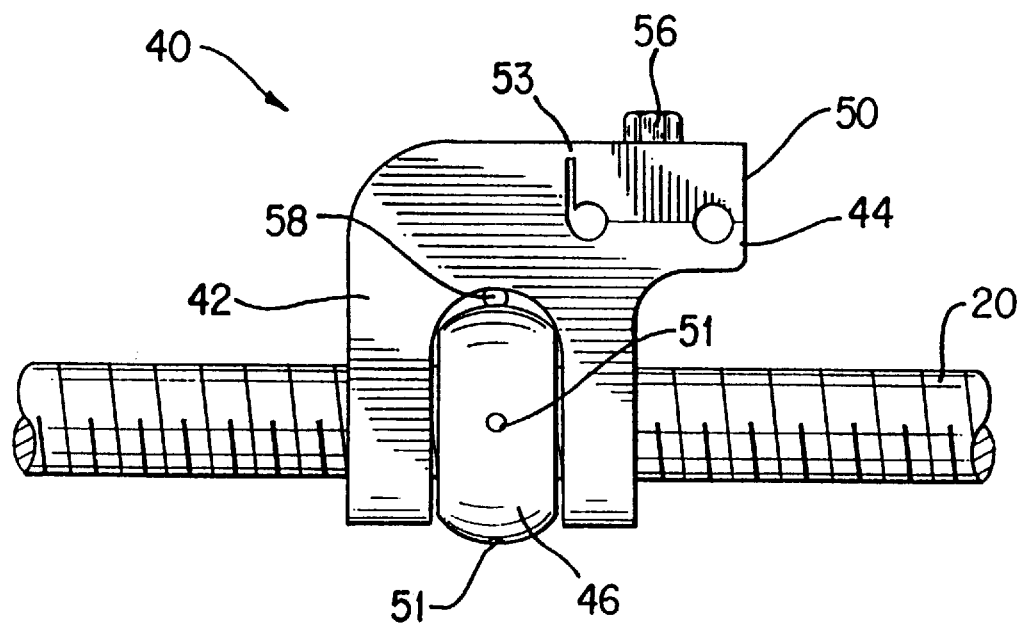
FIG. 8 is a side elevational view of the left bone-pin clamp of FIG. 1 as it is assembled onto the left arm.

The cap 50 has a screw-hole 58 throughout its thickness and a bottom surface 52 having two parallel diametrical grooves 54 along the entire width of the bottom surface 52 of a partial semi-cylindrical shape. The cap 50 is screwed to the rider 42 with the screw 56 which fits in the screw-hole 58 of the cap 50 and the screw-hole 49 of the rider 42 such that the diametrical grooves 43 of the rider 42 oppose the diametrical grooves 54 of the cap 50, thereby forming holes adapted to receive and retain bone-pins (not shown). The bone-pins are secured to the bone-pin clamp 40 by tightening the screw 56. As shown in FIG. 8, the cap 50 is preferably connected to rider 42 by a web 53.

As seen in FIGS. 7–8, the wheel 46 fits between the two cylindrical extensions 45 of the rider 42 such that the left arm 20 may fit through the cylindrical extensions 45 and the wheel 46. The wheel 46 is threaded along its inner circumference to mate with the threaded segments 24, 34 of the arms 20, 30. The left bone-pin clamp 40 moves along the left arm 20 as the wheel 46 is turned. To facilitate rotation of wheel 46, grooves or threads may be provided along its outer circumference. As the wheel 46 is rotated in one direction, the left bone-pin clamp 40 moves away from the central joint 80 (see FIG. 1), and conversely, as the wheel 46 is rotated in the opposite direction, the left bone-pin clamp 40 moves toward the central joint 80. Due to the mating of the left arm 20 with the D-shaped bores 47 of the cylindrical extensions 45, the left bone-pin clamp 40 is prevented from rotating about the left arm 20.

FIG. 9 shows the right bone-pin clamp 60 which is substantially identical to the left bone-pin clamp 40 except that the D-shaped bores 47 of the cylindrical extensions 45 are oriented differently (as shown) such that the extended portion 44 of the rider 42 of the right bone-pin clamp 60 is directed toward the central joint 80 when the right bone-pin clamp 60 is assembled onto the right arm 30.

The device of the present invention preferably has an indexing feature such that the bone-pin clamps can be moved along the arms in predetermined increments. One manner of providing this indexing feature is to provide a small bore 48 as shown in FIG. 9 in between the two cylindrical extensions 45 of the rider 42 which is fitted with a spring 55 and a small ball 58. The wheel 46 is provided with a number of indentations or depressions 51, in this embodiment, four, which are equally spaced along its outer circumferential surface which engage the ball 58 to provide a noticeable feel and/or sound such that turning the wheel 46 from one indentation 51 to the next produces a known linear adjustment along the length of the arms 20, 30. In addition, the flat-keyed segments 26 of each arm 20, 30 may be marked in the manner shown in order that the linear distance which the bone-pin clamps 40, 60 travel along the arms 20, 30 may be measured.

The device of the present invention also preferably is provided with a means to retain the bone-pin clamps on the arms. It is understood that many ways can be used to accomplish this feature such as altering the threaded segment at a point on the free end of the arms 20, 30 so that the threads on the wheel do not properly mesh with the threads on the arms 20, 30. Another means would be to provide a cap or other similar locking mechanism which is well-known in the art which would mate with the threads on the arms and act as a stop. The preferred means of retaining the clamps on the device of the present invention is to flare the ends of the arms 20, 30 so as to disrupt and damage the threads on the arms.

The central joint 80 also can be configured, as shown in FIG. 1, to retain bone-pins, for example, by having bores 71 for receiving the bone-pins and set screws 76 to retain the bone-pins in the bores 71 thereby fixing them to the central joint 80. It is to be understood that other ways can be used to retain the housing to the bone-pin such as, for example, using two plates with opposed diametrical grooves and clamping them together as described in reference to bone-pin clamps 40, 60. By configuring the central joint 80 to retain bone-pins, more than one distraction can occur, such as a distraction between the central joint 80 and arm 20 as well as the central joint 80 and arm 30. In addition, arms 20, 30 can be fitted with more than one bone-pin clamp each, such that multiple linear distractions, such as bone transport, can occur.

With no limitation intended and for illustrative purposes only, the central joint may be configured such that the center of rotation for each arm is within 5 mm of each other. The bone-pin clamps may be configured to retain either two 2 mm pins or one 3 mm pin and the diametrical grooves of the bone-pin clamps may be 10 mm apart. The device may allow for linear expansion of up to 20 mm along each arm and angular movement of up to 120°. It is contemplated that the device will be made from stainless steel with the angular-adjustment screws being formed of 455 H.T., the housing, arms, rider and cap formed of 17-4 and the gears and wheels formed of "Gall-Tough™" stainless steel made by Carpenter Technology Corporation for its wear resistance and self-lubricating characteristics.

While the device in its preferred form has been described with two arms, it is to be understood that the use of a single arm or multiple arms, i.e., more than two, is contemplated also. For example, the alternative embodiment of FIG. 10 illustrates an angular distraction device having a single arm.

Figure 10:
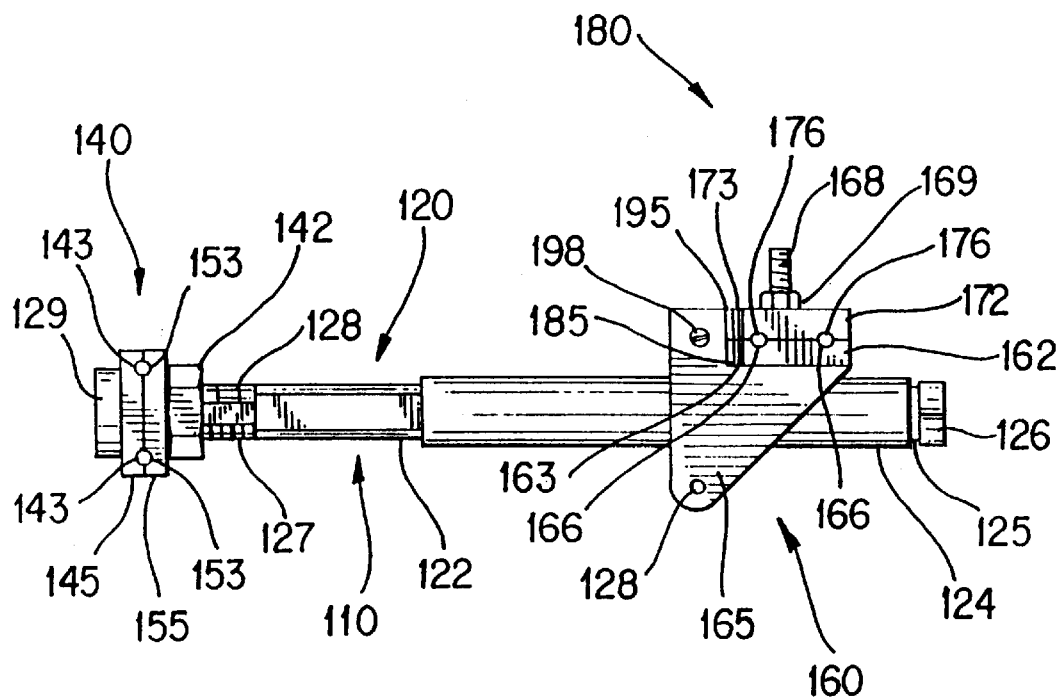
FIG. 10 is an alternative embodiment of the device according to the present invention.
Figure 11:
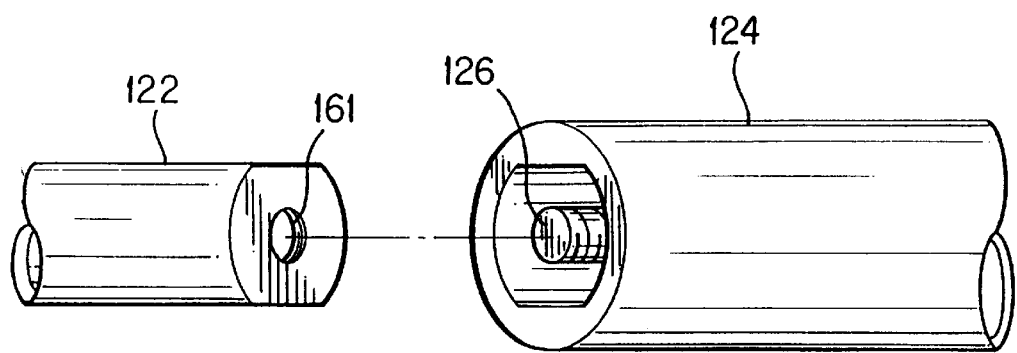
FIG. 11 is a perspective view of the arm of the device of FIG. 10 with portions broken away to show detail.

FIG. 10 shows device 110 which may be used to perform angular and linear distraction osteogenesis having an arm 120, a left bone-pin clamp 140, and a right bone-pin clamp 160 which has an angular-adjustment assembly 180. The arm 120 has a core member 122, a cylindrically-shaped telescoping member 124 which slides along core member 122 and a length-adjustment screw 126. The core member 122 has an internally threaded screw-hole 161 into which the length-adjustment screw 126 is fitted and mates. A collar 125 on the telescoping member maintains the length-adjustment screw 126 on the telescoping member so that it cannot move axially but allows the screw 126 to rotate freely. The length-adjustment screw is rotated in order to adjust the length of the arm 120. As shown in FIG. 11, the external shape of the core member 122 is non-circular in cross-sectional shape, and may be axisymetrical, and mates with the internal shape of the telescoping member 124 to prevent rotation of the telescoping member 124 about core member 122.

The left bone-pin clamp 140 has two plates 145, 155 each having a central hole 146, 156 and two diametrical grooves 143, 153 spaced in parallel and extending the entire width of plates 145, 155. The plates 145, 155 are configured on the arm so that the diametrical grooves 143 oppose diametrical grooves 153 to form holes adapted to receive and retain bone-pins (not shown).

The left bone-pin clamp 140 is fixed to the arm 120 so that it does not rotate or translate linearly along the length of the arm 120. The manner of fixing the left bone-pin clamp 140 to the arm 120 in FIG. 10 is by providing threads 127 along the end portion of the left end of the arm 120 and having a nut 142 to clamp the plates 145, 155 in place. In particular, nut 142 is fitted on the threaded portion 128 of the arm 120 and the plates 145, 155 are placed on arm 120 by fitting the threaded portion 128 through central holes 146, 156. The threaded portion 128 of arm 120 is non-circular in cross-section and has a smooth portion which does not have threads which prevent the plates from rotating. After the nut 142 and plates 145, 155 are placed on the arm 120, a stop 129 is provided at the left distal end of the arm 120 to prevent the plates 145, 155 from becoming detached from the arm 120. In operation, the bone-pins are placed in the holes formed by diametrical grooves 143, 153 and nut 142 is rotated to clamp and fix the bone-pins in the plates 145, 155 and the plates 145, 155 to the arm 120.

Figure 12:
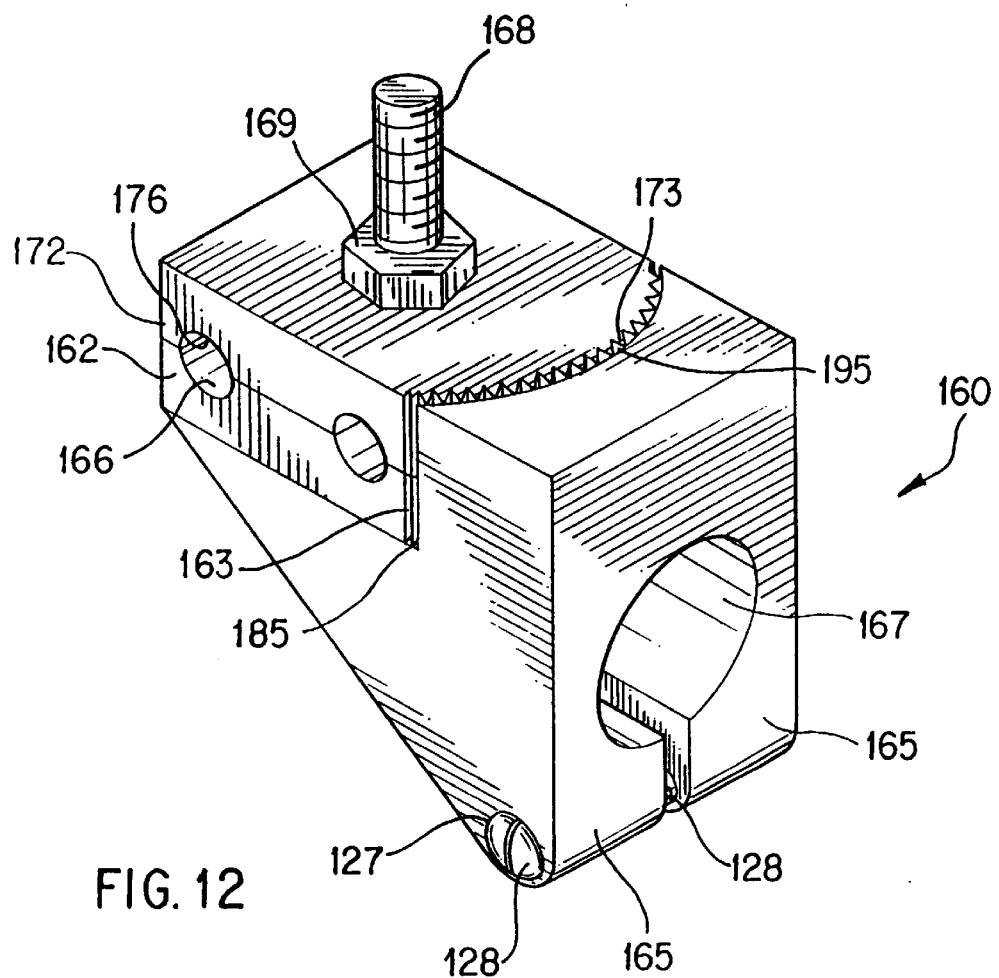
FIG. 12 is a perspective view of the bone-pin clamp of FIG. 10.

The right bone-pin clamp 160 in FIGS. 10 and 12 has two support members 165 and a cylindrically-shaped hole 167 formed between the support members 165 which receives the telescoping member 124 of arm 120 so that it can slide along the telescoping member 124. A threaded hole 127 extends through both support members 165 and receives a screw 128 which can be tightened to fix the bone-pin clamp 160 on the telescoping member 124. Loosening the screw 128 allows bone-pin clamp 160 to be positioned along the length of the telescoping member 124.

The right bone-pin clamp 160 also contains an angular-adjustment assembly 180. The angular-adjustment assembly 180 has an angular-adjustment screw 198 and two pin-clamp plates 162, 172. The angular-adjustment screw 198 is similar and may be identical to the angular-adjustment screw 88 described in FIGS. 4–5. The two pin-clamp plates 162, 172 have a circular shape along a portion of their perimeters 163, 173 and are formed with "V-shaped" teeth 185, 195 similar to those described in FIGS. 4–6. The angular-adjustment screw 198 and "V-shaped" teeth 185, 195 are configured to cooperate and mesh with each other as described earlier in reference to angular-adjustment screw 88 and gear 84 in FIGS. 4–6 such that rotating screw 198 angularly adjusts plates 162, 172. The pin-clamp plates 162, 172 adjust angularly in unison.

Pin-clamp plates 162, 172 are also formed with two diametrical grooves 166, 176 each set spaced in parallel and extending the entire width of the pin-clamp plates 162, 172.

Each pin-clamp plate 162, 172 also is provided with a screw-hole 167 extending throughout its thickness and adapted to receive a threaded pin 168. The pin-clamp plates 162, 172 are arranged on threaded pin 168 so that diametrical grooves 166 oppose diametrical grooves 176 to form holes to hold bone-pins. A nut 169 is threaded on threaded pin 168 to press the plates 162, 172 together to hold the bone-pins. The threaded pin 168, however, allows the plates 162, 172 to angularly adjust about the pin 168 when the plates are tightened together by nut 196.

Figure 13:
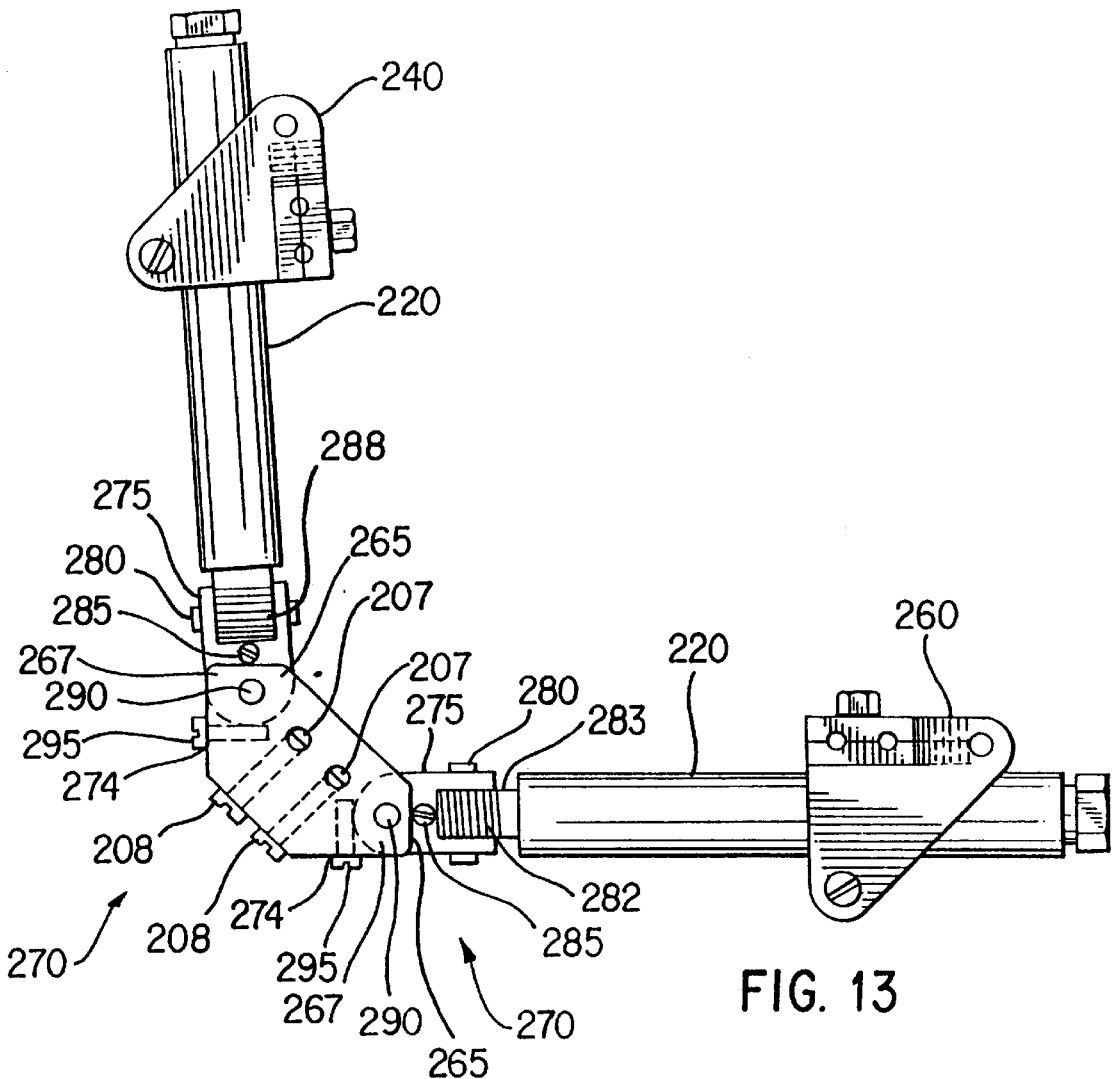
FIG. 13 is a side elevational view of an alternative embodiment of the device of the present invention which provides for two distractions.

The alternative embodiment shown in FIG. 13 can be used to perform two distractions and has two arms 220, a central joint 270 and bone-pin clamps 240, 260. The arms 220 are identical and each has a core member, a telescoping member which slides along the core member and a length-adjustment screw as described above in reference to FIGS. 10 and 11. Each bone-pin clamp 240, 260 also is the same as bone-pin clamp 160 described in FIGS. 10 and 12.

Figure 14:
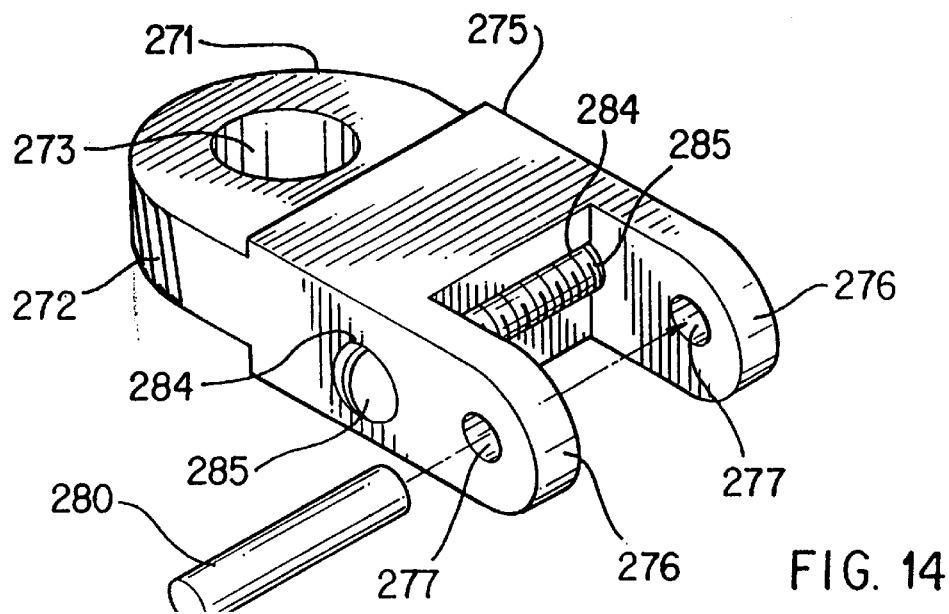
FIG. 14 is a perspective view of the angular-adjustment support piece of FIG. 13.

Both arms 220 are connected to central joint 270 via angular-adjustment support piece 275 as shown in FIG. 14. The central joint 270 has two bone-pin holes 207 to receive bone-pins and two set screws 208 to hold the bone-pins within the holes 207 and fix them to the central joint 270.

The angular-adjustment support piece 275 has two U-shaped support extensions 276 with circular holes 277 configured to receive axle 280 and a U-shaped gear section 271 having a portion which is of circular perimeter. The gear section 271 has a hole 273 and "V-shaped" teeth 272, as previously described with reference to FIGS. 4–6, formed along its circular perimeter. The angular-adjustment support piece 275 has a bore 284 which receives angular-adjustment screw 285. A pin and groove similar to that described in reference to FIGS. 4–6 is used to retain the screw 285 in the angular-adjustment support piece while allowing it to rotate.

The arms 220 are provided with ends which have a disk-like circular perimeter 283 with "V-shaped" teeth 282 formed therein similar to gear section 271 of the angular support piece 275. The arm 220 is provided with a bore 284 (not shown) configured to receive axle 280. The circular perimeter 283 of arm 220 is inserted in between the U-shaped support extensions 276 of the angular-adjustment piece 275 so that bore 284 is aligned with circular holes 277 and axle 280 is inserted therein. The arm 220 can be fixed to the axle 280 in a number of ways and in this embodiment, is fixed thereto by drilling a hole through the circular perimeter 283 and axle 280 and using a pin similar to that used in the preferred embodiment described in FIGS. 1–6. The "V-shaped" teeth 282 on the arm 220 mesh and cooperate with the threads on angular-adjustment screw 285 so that turning screw 285 angularly adjusts or rotates the arm 220 with respect to the angular-adjustment piece 275.

The central joint 270 has two sets of U-shaped supports 265, one set on each end which is used to connect the annular adjustment support piece 275 to the central joint 270 in the same manner in which arm 220 is connected to the angular-adjustment support piece 275. In particular, the U-shaped supports 265 are provided with circular holes 267 configured to receive cylindrical axle 290. The gear section 271 of the angular-adjustment support piece 275 is received in the central joint 270 between the set of U-shaped supports 265. Axle 290 is inserted through hole 267 in the central joint 270 and hole 273 in the angular-adjustment support piece 275. A pin, similar to pin 7 in FIG. 4, is used to secure the angular-adjustment support piece 275 to the central joint 270.

In addition, the central joint 270 has two bores 274 formed on its ends and in proximity of the U-shaped supports 265 for receiving angular-adjustment screws 295. The angular-adjustment screws are received in bores 274 and retained therein by a pin and groove as described with reference to FIGS. 4–5. The threads on angular-adjustment screw 295 cooperate and mesh with the "V-shaped" grooves 272 on the angular-adjustment support piece 275 so that rotating the screw 295 angularly adjusts the angular-adjustment support piece 275.

It is to be understood that FIG. 12 has been described with reference to a double angular-adjustment mechanism but that a single angular-adjustment mechanism can be provided by attaching the arm with its disk-like circular perimeter and "V-shaped" teeth on its end directly in between the U-shaped extensions 265 on the central joint 270 with an axle. It is understood also that only one arm 220 can be used with either the single or double angular-adjustment mechanism and/or with or without the angular-adjustment mechanism incorporated in the bone-pin clamps 240, 260.

Figure 15:
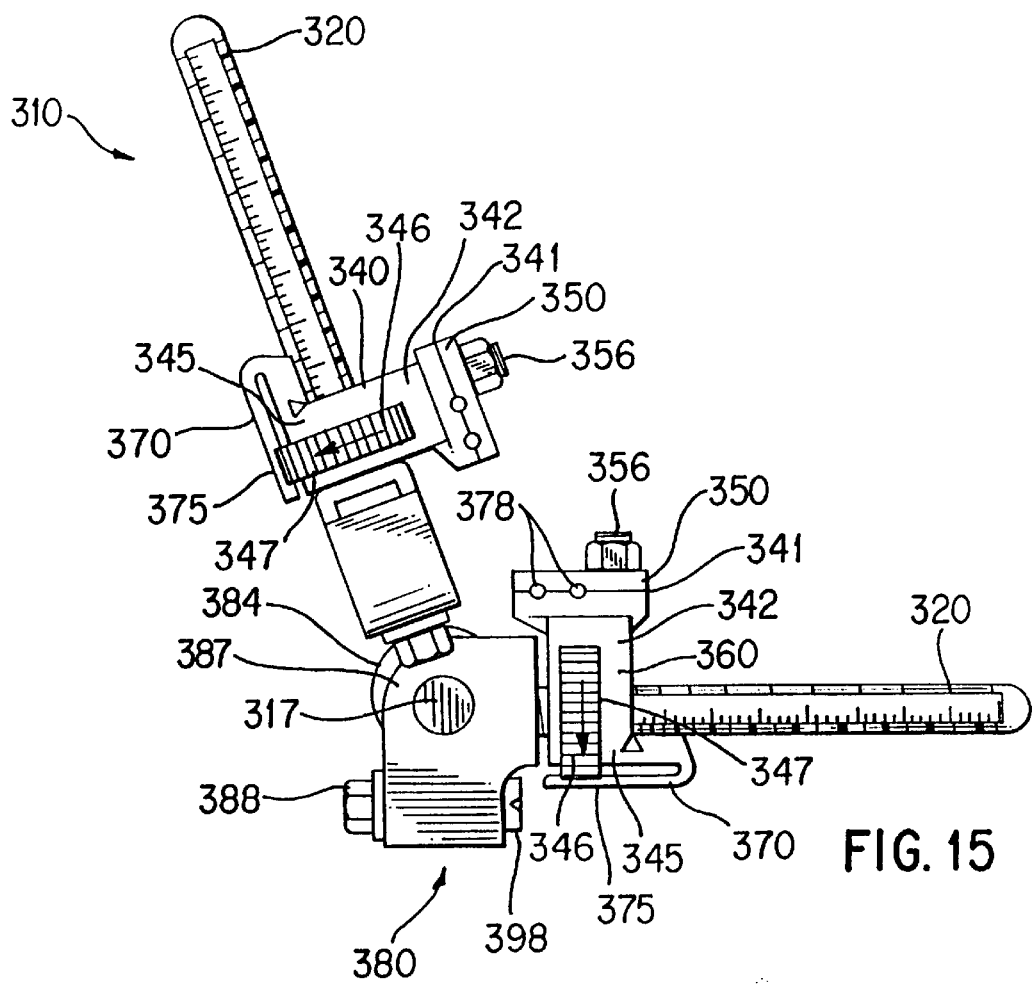
FIG. 15 is a side elevational view of an alternative embodiment of the present invention.

In the alternative embodiment in FIG. 15, the device 310 is substantially the same as the device 10 except for minor differences to be described. In the embodiment of FIG. 15, the arms 320 are fixed to supports 387. Each support 387 contains and retains angular-adjustment screws 388, 389 in the manner described with reference to FIGS. 4–5. Gears 384, 385 (not shown) are provided and are both semicircular in shape and fixed to each other. Supports 387 are retained on gears 384, 385 by cylindrical axles 317, 327 (not shown) which allow the supports 387 and arms 320 to rotate about their respective gears 384, 385. The gears are oriented in different planes and in the embodiment of FIG. 15 are perpendicular to each other so that the arms 320 rotate in perpendicular planes.

The gears 384, 385 are provided with "V-shaped" teeth as shown and described in reference to FIGS. 4–6 which mate with the standard machine threads on respective angular-adjustment screws 388, 398 such that rotating the screws angularly adjusts arms 320 about the respective gears 384, 385.

The bone-pin clamps 340, 360 are similar to the bone-pin clamps 40, 60 in the preferred embodiment. However, the bone-pin clamps 340, 360 in FIG. 15 have U-shaped clip locks 370 to prevent the wheel 346 from spinning and thereby maintain the bone-pin clamps 340, 360 in a fixed position relative to the arms 320, 330. As shown in FIG. 15, each U-shaped clip lock 370 is attached at one end to the cylindrical extension 345 and extends across and in contact with the wheel 346. The shape and configuration of the U-shaped clip lock is such that it is biased toward the wheel 346. The wheel 346 is provided with grooves 347 and the U-shaped clip lock has an extension 375 where it contacts the wheel 346 in order to mate with a groove 347 and hold the wheel in place. The biasing force between the free end of each U-shaped clip lock 370 and the wheel 346 is such that the wheel 346 will be held firmly in place, but may be overcome if sufficient force were applied to the wheel 346.

In addition, the portion of the bone-pin clamps 340, 360 which hold the bone-pins is slightly different in the embodiment of FIG. 15 from the embodiment of FIGS. 7–9. The recessed surface 341 extends throughout the rider 342 and the cap 350 covers the entire top of the rider 342. The screw 356 is off-set from bone-pin grooves 378 and secures the cap 350 to the rider 342 to secure the bone-pin(s).

Figure 16:
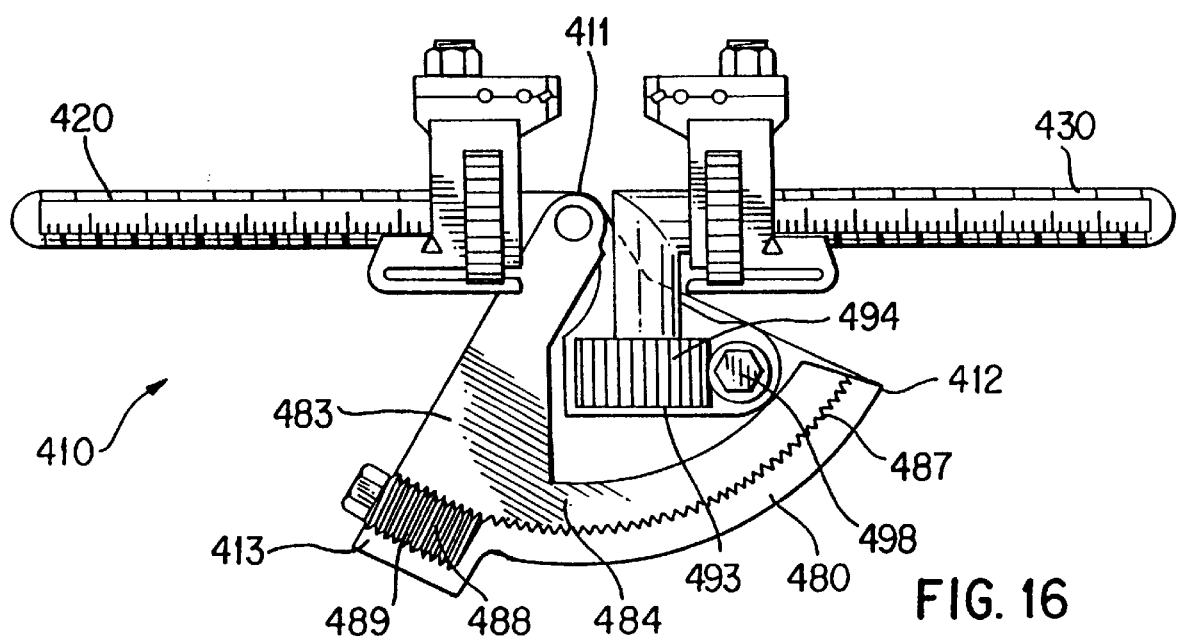
FIG. 16 is an alternative embodiment of the device showing an alternative configuration of the central joint shown in cross-section.

In the alternative embodiment in FIG. 16, the device 410 is substantially the same as the preferred embodiment shown in FIG. 1, except for minor differences in the left arm 420 and the central joint 480 to be described. The central joint 480 in FIG. 16 is shown in cross-section to reveal the inner components. There is only one U-shaped support 493 in the central joint 480 which is configured such that angular adjustments may be made to the right arm 430 via the angular-adjustment screw 498 corresponding with gear 494 as substantially described in the description of the embodiment of FIG. 1.

However, in lieu of the second U-shaped supports, the central joint 480 shown in FIG. 16 has an extended sandwich support 483 which has a pivot corner 411, an adjustment corner 413 and a distal corner 412. The sandwich support 483 has an inner layer 414 and an outer layer 415 and houses the angular-adjustment screw 488 at the adjustment corner 413 and a V-gear 484 between the inner layer 414 and the outer layer 415. The inner layer 414 is the mirror image of the outer layer 415. The V-gear 484 has teeth or grooves 487 and is retained within the sandwich support by an axle 417 at the pivot corner 411. The threads 489 of the screw 488 mate with the teeth 487 on the V-gear 484. Angular adjustments may be made to the left arm 420 by rotating the angular-adjustment screw 488 which rotates the V-gear 484 which is attached to the left arm 420. As the V-gear 484 is rotated, it moves in and out of the sandwich support 483. The configuration of the central joint 480 minimizes the distance between the pivoting points of the two arms and places the centers of rotation as close as possible.

Figure 17:
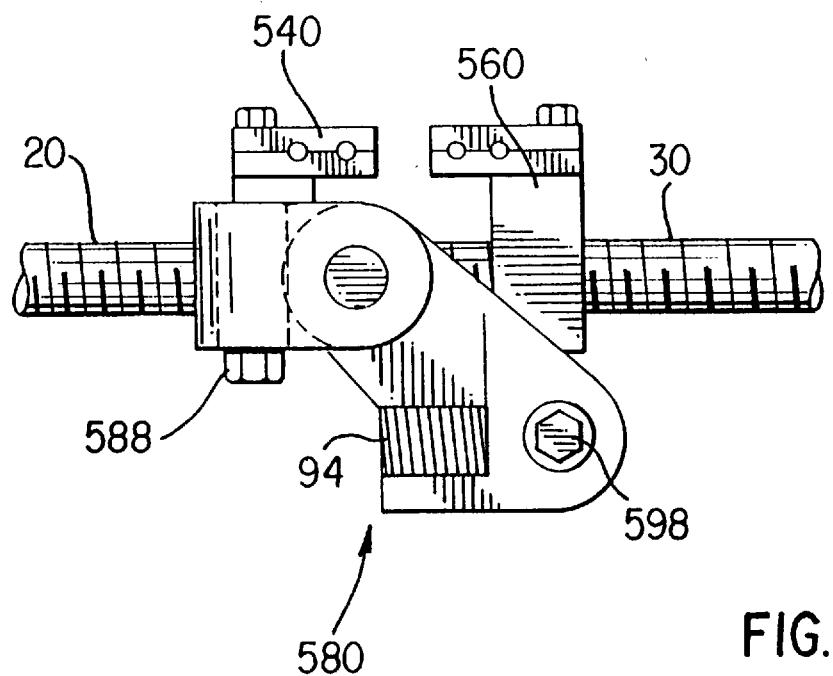
FIGS. 17 and 18 are side elevational views of alternative embodiments of the device of the present invention.

The alternative embodiment shown in FIG. 17 is substantially the same as the device described in FIG. 1. However, the central joint 580 is structured such that the angular-adjustment screws 588, 598 are perpendicular to one another. The bone-pin clamps 540, 560 are similar to those shown in FIG. 15.

Figure 18:
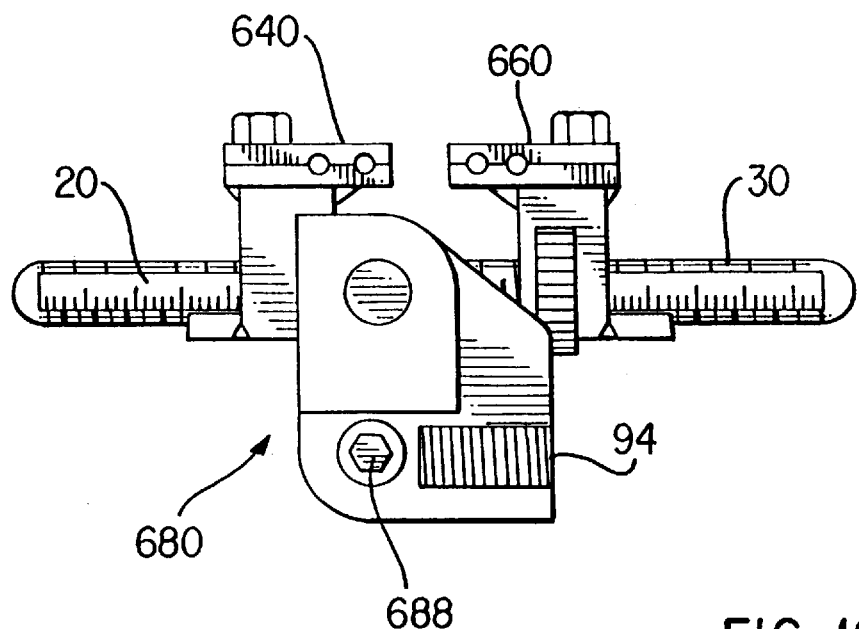

The alternative embodiment shown in FIG. 18 is substantially the same as the embodiment of FIG. 17. However, the central joint 680 is configured such that the angular-adjustment screw 688 fits within the central joint 680 on the other side of the gear 684. This configuration makes the central joint 680 in FIG. 18 more compact than the central joint 580 in FIG. 17.

Figure 19:
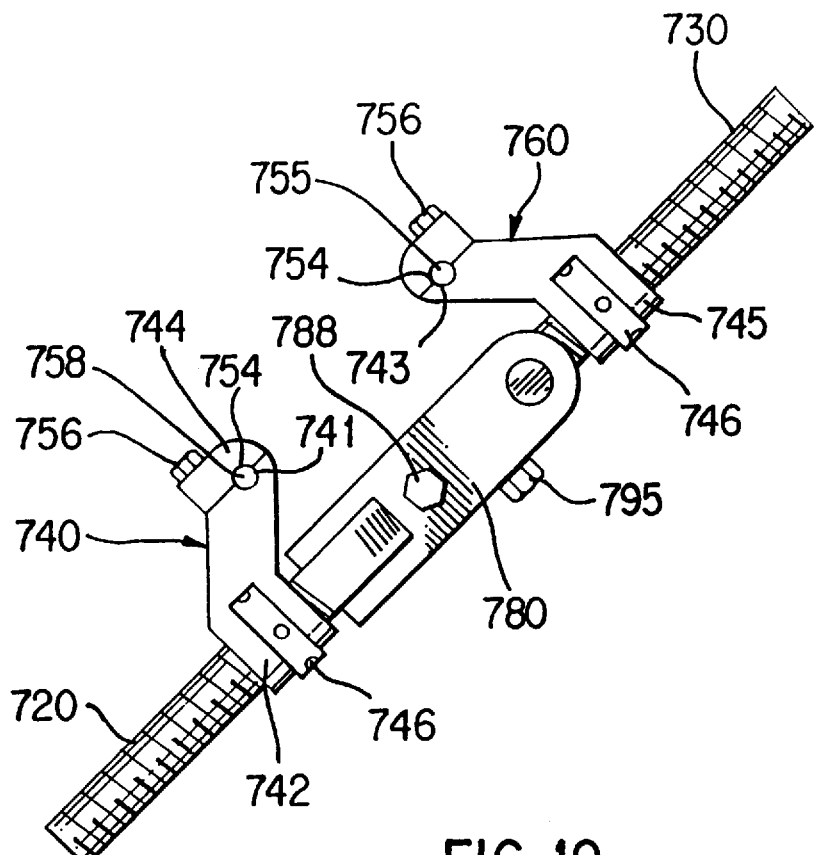
FIG. 19 is an alternative embodiment of the device of the present invention showing an elongated central joint.
Figure 20:
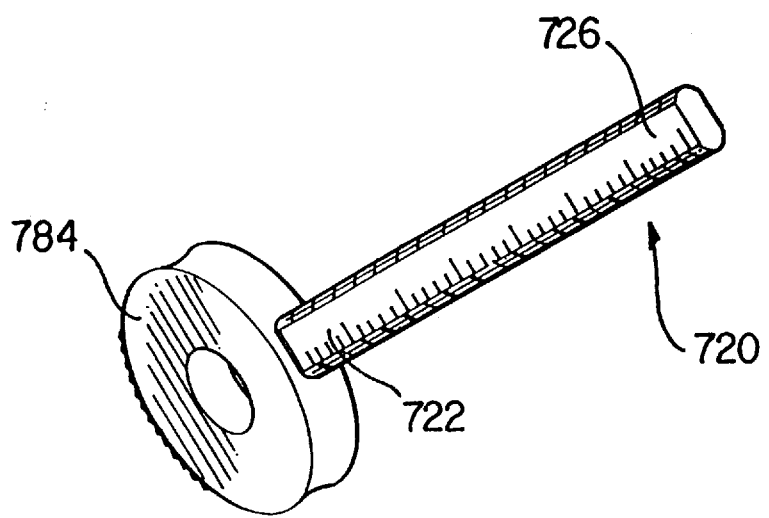
FIG. 20 is a perspective view of the arms of FIG. 19.

In the alternative embodiment in FIG. 19, the arms 720, 730 are identical as shown in FIG. 20, wherein each head segment is connected directly to the gear 784. The arms 720, 730 rotate about axes of rotation such that the planes of rotation of each arm are perpendicular to each other. The central joint 780 is structured such that the screws 788, 798 are located in a different position in relation to the gear and in particular, are perpendicular to one another.

The bone-pin clamps 740, 760 of FIG. 19 are essentially similar to the bone-pin clamps 40, 60 of FIG. 1 in that the cylindrical extensions 745, D-shaped bores 747 and wheel 746 are the same. However, because of the extended linear nature of the central joint 780, the extended portions 744 of the bone-pin clamps 740, 760 must extend further away from the cylindrical extensions 745 than the extended portions 44 of the bone-pin clamps 40, 60 in order that the bone-pin clamps 740, 760 may be fitted onto bone-pins which are placed close together, as at the onset of distraction.

In addition, the recessed surface 741 of rider 742 has a "V-shaped" groove 743, and the cap 750 has a semicircular groove 754. It is to be understood that the cross-sectional shapes of grooves 743, 754 may be reversed. The "V-shaped" groove 743 of the rider 742 opposes the semicircular groove 754 to form an adjustable bore 758 in the bone-pin clamps 740, 760 to retain bone-pin(s) of varying size, such as either a 2 mm or 3 mm bone-pin. The bone-pin clamps 740, 760 are secured to a bone-pin by aligning the bone-pin in adjustable bore 758 and tightening the screw 756.

Figure 21:
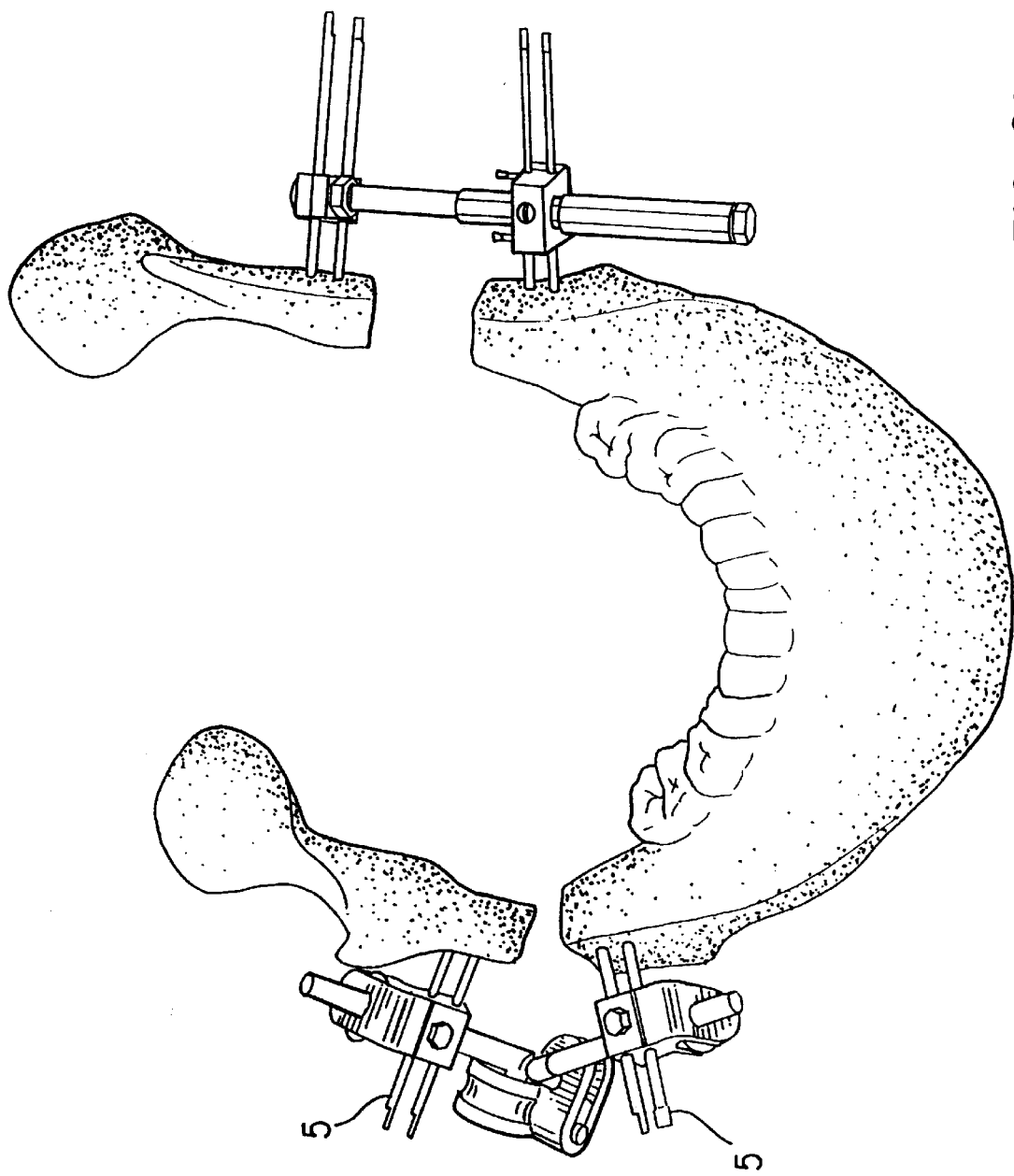
FIG. 21 is a perspective view of the device of the present invention and a prior art device as they would be used on the human mandible.

FIG. 21 shows the device of the present invention 10 on the left as compared to a known linear distraction device on the right as they would be used to perform distraction osteogenesis of a human mandible. The device of the present invention finds particular utility where angular distraction is necessary in order to bend bone or form curved bone such as in the mandible in order to round out the face and to provide a proper bite. The ability to angularly adjust the arms in relation to each other as provided by the device shown on the left side in FIG. 21 allows the bone to be curved or bent into its proper shape. The advantage of the device of the present invention is that it can perform distraction osteogenesis both linearly and angularly, both independently and simultaneously, and depending upon the embodiment, can perform linear and angular distraction about two independent axes defining differently oriented planes thereby providing three-dimensional distraction.

The device of the present invention is used by drilling at least one bone-pin hole on both sides of the segmented bone, or where an osteotomy is intended to be performed, in a manner known in the art. The bone-pins are inserted into the drilled bone-pin holes such that a portion of each bone-pin extends from the bone. In particular, bone-pins 5 are inserted and fixed in a first side of a segmented bone and bone-pins 5 are inserted and fixed in a second side of a segmented bore and the distraction device is attached. The bone-pin clamps are fitted onto the external segments of the bone-pins such that at least one bone-pin fits through each bone-pin clamp on the arm(s) of the device. A template can be used in order to adjust the device before mounting it onto the bone-pins. With reference to the distraction device 10 of FIG. 1, the bone-pin clamps 40, 60 are then tightened such that the device is firmly attached to the bone-pins.

Linear distraction is effected by gradually moving the bone-pin clamps 40, 60 a distance along the arms 20, 30 by turning wheel 46. It is contemplated that linear distraction of approximately 1 millimeter per day will occur by undergoing half-millimeter distractions twice a day. It is contemplated further that these adjustments will be made by the patient, the parent or other person not necessarily having any medical experience.

Angular distraction is effected by making small angular adjustments to the arms 20, 30 of the device by turning screws 88, 98. It is further contemplated that the patient, parent, or other individual, not necessarily having any medical experience, will angularly adjust the device according to the physician's instructions. It is understood that pure angular distraction may occur without undergoing any linear distraction osteogenesis. The angular adjustment of the arm occurs gradually, incrementally, precisely and in a controlled predetermined manner over a period of time so that the bone remains healthy and the blood vessels and nerves remain intact. Further, it is understood that linear and angular adjustments may occur concurrently or separately.

The invention has been described herein in considerable detail, both as to the preferred embodiment and several alternative embodiments, in order to enable those skilled in the art to manufacture and use the device according to the present invention. However, it is understood that this invention may be carried out by different devices having various modifications to the embodiments described herein without departing from the scope of the invention itself.

We claim:

1. A device for achieving angular distraction osteogenesis on a segmented piece of bone, comprising:
    a central joint;
    a first arm and a second arm having two respective axes of rotation and connected to the central joint;
    means for securing a first side of the segmented bone to the first arm;
    means for securing a second side of the segmented bone to the second arm;
    means for independently and angularly adjusting the first arm relative to the second arm comprising a first gear having a radius, and a means for rotating the first gear; and
    means for independently and angularly adjusting the second arm relative to the first arm comprising a second gear having a radius, and a means for rotating the second gear,
    wherein the shortest distance between the axes of rotation of the first and second arms is less than the sum of the first gear radius and the second gear radius.

2. The device according to claim 1 wherein the means for rotating the first gear comprises a first angular-adjustment screw and the means for rotating the second gear comprises a second angular-adjustment screw.

3. The device according to claim 2 wherein at least one angular-adjustment screw is self-locking to prevent undesirable angular movement.

4. The device according to claim 2, wherein the distance between the axes of rotation of the first and second arms is from about 0 mm to about 10 mm and the two angular-adjustment screws are aligned along the same axis.

5. The device according to claim 1 further comprising means for linearly translating the position of at least one bone securing means along the length of its respective arm.

6. The device according to claim 5 further comprising means for measuring the linear translation of the bone securing means along the length of its respective arm.

7. The device according to claim 6 wherein linear translation measuring means comprises scale markings along the length of the arm.

8. The device according to claim 5 further comprising means to lock the linear translation means to prevent undesired linear movement of the bone securing means along the length of the arm.

9. The device according to claim 5 further comprising means to retain at least one bone securing means on its respective arm.

10. The device according to claim 1 configured and adapted for use as an external bone-distraction device.

11. The device according to claim 1 wherein the means to independently and angularly adjust at least one arm is contained within the central joint and comprises at least a rear and means to rotate said gear.

12. The device according to claim 2 wherein the first angular-adjustment screw is in direct meshing contact with the first rear and the second angular-adjustment screw is in direct meshing contact with the second gear.

13. The device according to claim 12 wherein at least one angular-adjustment screw has standard machine threads and at least one gear has V-shaped teeth configured to mesh with the machine threads such that rotating the screw rotates said gear.

14. The device according to claim 1 wherein the first arm angularly adjusts in a differently oriented plane than the second arm.

15. The device according to claim 14 wherein the first arm angularly adjusts in a plane which is perpendicular to the plane formed by the angular adjustment of the second arm.

16. The device according to claim 14 wherein the two angular-adjustment screws are aligned along the same axis.

17. The device according to claim 1 wherein the central joint, first arm and second arm each contain means for securing bone-pins to a segment of bone.

18. The device according to claim 17 further comprising a second means for securing bone-pins to the first arm.

19. A device according to claim 1, wherein the distance between the axes of rotation of the first and second arms is from about 0 mm to about 10 mm.

20. A device according to claim 1, wherein the first arm is substantially L-shaped.

21. A device according to claim 1, wherein the first arm is angularly adjustable in a range of about 0° to about 135°.

22. The device according to claim 21 wherein the first arm is angularly adjustable in a range of about 0° to about 120°.

23. A device for achieving distraction osteogenesis, comprising:
    a first elongated support member;
    a second elongated support member;
    a means for securing at least one bone-pin to the first elongated support member;
    a means for securing at least one bone-pin to the second elongated support member; and
    an adjustment means for independently and angularly adjusting the first elongated support member relative to the second elongated support member in order to bend the bone in a manner that the bone tissue remains healthy and the blood vessels and nerve endings remain intact during the bending process, wherein the adjustment means comprises a first gear having "V-shaped" teeth and a first angular-adjustment screw having standard machine threads, the first angular-adjustment screw in contact and meshing with the "V-shaped" teeth of the first gear such that rotating the first angular-adjustment screw angularly adjusts the first elongated support member.

24. A device according to claim 23 wherein the adjustment means further comprises a second gear having "V-shaped" teeth and a second angular-adjustment screw having standard machine threads, the second angular-adjustment screw in meshing contact with the "V-shaped" teeth of the second gear such that rotating the second angular-adjustment screw angularly adjusts the second elongated support member.

25. The device according to claim 24 wherein the first elongated support member angularly adjusts in a first plane and the second elongated support member angularly adjusts in a second plane, the first plane being oriented differently from the second plane.

26. A device according to claim 24, wherein the first and second elongated support members have two respective axes of rotation, each of the first and second gears has a respective radius, and wherein the shortest distance between the two respective axes of rotation is less than the sum of the first gear radius and the second gear radius.

27. The device according to claim 25 wherein the first plane of angular adjustment is perpendicular to the second plane of angular adjustment.

28. The device according to claim 27 wherein the two angular-adjustment screws are arranged along the same axis.

29. The device according to claim 23 further comprising means for linearly adjusting the position of at least one of the bone-pin securing means along the length of its respective elongated support member.

30. The device according to claim 29 wherein the means for securing the bone-pin(s) to the first elongated support member comprises a bone-pin clamp having two extensions provided with holes, a wheel provided with a hole and means for securing the bone-pin(s) to the bone-pin clamps, the wheel being fitted between the two extensions and the arm fitted in the holes provided in the two extensions and the wheel.

31. The device of claim 30 wherein the means for linearly adjusting the bone-pin securing means comprises threaded portions on the respective elongated support member and threads on the wheel, the threaded portions on the elongated support member mating with the threads on the wheel to provide linear movement of the bone-pin securing means along its respective elongated support member.

32. The device according to claim 31 wherein the bone-pin clamp has a spring with a ball provided thereon in a bore located between the two extensions and the wheel has equally-spaced predetermine indentations along its outer circumference, the indentations configured to releasably mate with the ball as the wheel is turned.

33. The device of claim 32 wherein the bone-pin clamp comprises means for holding various sized bone-pins.

34. A device according to claim 23, wherein the first elongated support member is angularly adjustable in a range of about 0° to about 135°.

35. The device according to claim 34 wherein the first elongated support member is angularly adjustable in a range of about 0° to about 120°.

36. The device according to claim 35, wherein the first elongated support member is substantially L-shaped.

37. The device according to claim 36, wherein the angular-adjustment screws are aligned along the same axis.

38. An external bone-lengthening device to perform three-dimensional distraction osteogenesis comprising:

a first arm having a head segment and a shaft;

a second arm having a head segment and a shaft;

a central joint having two angular-adjustment screws, two supports and two gears, the first support forming an axis of rotation for the first arm and configured to receive the first gear and the head segment of the first arm, and the second support forming an axis of rotation for the second arm and configured to receive the second gear and the head segment of the second arm, the axis of rotation of the first arm being different from the axis of rotation of the second arm, and the screws are arranged to be adjacent to and in meshing contact with their respective gears such that turning the first screw turns the first gear and angularly adjusts the first arm and turning the second screw turns the second gear and angularly adjusts the second arm;

a first bone-pin clamp fitted on and linearly adjustable along the length of the first arm; and a second bone-pin clamp fitted on and linearly adjustable along the length of the second arm, wherein each bone-pin clamp comprises:

two cylindrical extensions provided with holes;

a wheel provided with a hole; and means for securing the bone-pins to the bone-pin clamps, wherein the wheel is fitted between the two cylindrical extensions and the arm is fitted in the holes provided in the two cylindrical extensions and the wheel.

39. The device according to claim 38 wherein the axis of rotation of the first arm is perpendicular to the axis of rotation of the second arm.

40. The device according to claim 38 wherein the first and second arms are integrally connected to their respective gears.

41. The device according to claim 38 further comprising means for retaining at least one of the bone-pin clamps on at least one of the arms.

42. The device according to claim 41 wherein the bone-pin clamp retaining means includes a locking cap secured to the shaft of the arm to prevent the bone-pin clamp from falling off the arms.

43. The device according to claim 39 wherein the shafts of the first and second arms have threads and the inner surface of the wheels have threads, the threads of the arms mating with the threads of the wheels to provide linear translation of the bone-pin clamps along the length of the arms.

44. The device according to claim 43 wherein the wheel of at least one of the bone-pin clamps is provided with indentations along equal, predetermined angular positions along its circumference at least one of which mates with a protrusion on the cylindrical extension of the bone-pin clamp so that predetermined linear adjustments of the bone-pin clamp can be determined.

45. The device according to claim 39 further comprising means to angularly orient the bone-pin clamps on the arms so that both clamps are properly oriented with the bone-pins extending from the bone.

46. The device according to claim 45 wherein the means to angularly orient the bone-pin clamps include the first and second arms of noncircular cross-section cooperating with respective noncircular holes in the cylindrical extensions of the bone-pin clamps.

47. The device according to claim 39 wherein the means for securing the bone-pin(s) to the bone-pin clamps comprises:

a bone-pin clamp portion having at least one semicircular groove;

a cap plate having a "V-shaped" groove;

and a screw for attaching the cap plate to the bone-pin clamp portion, the cap plate being adjustably secured so that the semicircular groove opposes the "V-shaped" groove to provide a hole which is adapted to secure the bone-pin.

48. A device according to claim 38, wherein each of the first and second gears has a respective radius and the shortest distance between the axes of rotation of the first and second arms is less than the sum of the first gear radius and the second gear radius.

49. The device according to claim 38, wherein the two gears have "V-shaped" teeth and the two angular-adjustment screws have standard machine threads, the two angular-adjustment screws in contact and meshing with the "V-shaped" teeth of the two gears respectively such that rotating the first angular-adjustment screw angularly adjusts the first arm and rotating the second angular-adjustment screw angularly adjusts the second arm.

50. The device according to claim 38 wherein the first arm is angularly adjustable in a range of about 0° to about 135°.

51. A device according to claim 50, wherein the first arm is angularly adjustable in a range of about 0° to about 120°.

52. A device according to claim 38, wherein the two angular-adjustment screws are arranged along the same axis.

53. A device capable of performing both linear osteogenesis and angular osteogenesis, so as to make a bone-shaping correction in a three-dimensional curve while said device is in place on a patient, said device comprising:
   (1) a center piece;
   (2) a first arm having a first longitudinal axis and a first lever arm having a first lever arm axis substantially perpendicular to said first longitudinal axis;
   (3) a first clamp attached to said first arm for holding first bone pins, said first clamp being linearly adjustable along said first longitudinal axis;
   (4) a second arm having a second longitudinal axis and a second lever arm having a second lever arm axis substantially perpendicular to said second longitudinal axis;
   (5) a second clamp attached to said second arm for holding second bone pins, said second clamp being linearly adjustable along said second longitudinal axis,
wherein said first arm and said second arm are positioned within said center piece and rotatable and lockable independently of each other in separate independently selected positions so as to form an incremental angle modifier for modifying the angle α between said first bone pins in said first clamp and said second bone pins in said second clamp and for modifying the angle between the first and second longitudinal axes.

54. A device according to claim 53, wherein said first lever arm axis is substantially perpendicular to said second lever arm axis.

55. A device according to claim 54, wherein said first arm is rotatable within a plane $P_1$ and at an angle β between about 0° and about 180° as measured from said second arm within said plane $P_1$ and wherein said second arm is independently rotatable within a plane $P_2$ and at an independent angle γ between about 0° and about 180° as measured from said first arm within said plane $P_2$ and wherein said plane $P_1$ is substantially perpendicular to said plane $P_2$.

56. A device according to claim 55 wherein said second lever arm axis and said first lever arm axis are spaced only slightly apart at a distance of only about 0 mm to about 10 mm, and wherein said angle γ and said angle β are independent and lie between about 0° to about 135°.

57. A device according to claim 53, wherein the first arm is angularly adjustable in a range of about 0° to about 135°.

58. The device according to claim 57, wherein the first and second arms are angularly adjustable in a range of about 0° to about 120°.

59. The device according to claim 53, wherein the incremental angle modifier comprises at least one gear with "V-shaped" teeth and at least one angular adjustment screw with standard machine threads which are arranged to contact and mesh with the "V-shaped" teeth on the gear such that rotating the angular adjustment screw angularly adjusts at least one of the arms.

60. A device for achieving distraction osteogenesis, comprising:
   a first elongated support member having an axis of rotation;
   a second elongated support member having an axis of rotation;
   a means for securing at least one bone-pin to the first elongated support member, said securing means comprising a bone-pin clamp having two extensions provided with holes, a wheel provided with a hole and means for securing the bone-pin(s) to the bone-pin clamp, the wheel being fitted between the two extensions and the elongated support member fitted in the holes provided in the two extensions and the wheel, wherein the bone-pin clamp has a spring with a ball provided thereon in a bore located between the two extensions and the wheel has equally-spaced predetermined indentations along its outer circumference, the indentations configured to releasably mate with the ball as the wheel is turned;
   a means for securing at least one bone-pin to the second elongated support member;
   a means for independently and angularly adjusting at least one of the first and second elongated support members relative to the other support member in order to bend the bone in a manner that the bone tissue remains healthy and the blood vessels and nerve endings remain intact during the bending process; and
   a means for linearly adjusting the position of at least one of the bone-pin securing means along the length of its respective elongated support member, comprising threaded portions on the respective elongated support member and threads on the wheel, the threaded portions on the elongated support member mating with the threads on the wheel to provide linear movement of the bone-pin securing means along the respective elongated support member.

61. The device of claim 60 wherein the bone-pin clamp comprises means for holding various sized bone-pins.

62. The device according to claim 60, wherein the distance between the axes of rotation of the first and second support members is from about 0 mm to about 10 mm.

63. A device for achieving angular distraction osteogenesis on a segmented piece of bone, comprising:
   a first arm;
   a second arm connected to the first arm;
   means for securing a first side of the segmented bone to the first arm;
   means for securing a second side of the segmented bone to the second arm;
   a first gear and a first angular-adjustment screw for angularly adjusting the first arm relative to the second arm; and
   a second gear and a second angular-adjustment screw for angularly adjusting the second arm relative to the first arm, wherein the two angular-adjustment screws are aligned along the same axis.

64. The device according to claim 63, wherein the first gear has "V-shaped" teeth and the first angular-adjustment screw has standard machine threads which are arranged to mesh with the "V-shaped" teeth on the first gear and rotate the first arm in a range of about 0° to about 135°.

65. The device according to claim 64, wherein the second gear has "V-shaped" teeth and the second angular-adjustment screw has standard machine threads which are arranged to mesh with the "V-shaped" teeth on the second gear and rotate the second arm in a range of about 0° to about 135°.

66. A device for achieving angular distraction osteogenesis on a segmented piece of bone, comprising:
   a central joint;
   a first arm and a second arm connected to the central joint;
   at least two bone-pins;

a first bone-pin clamp positioned on the first arm for securing at least one bone-pin to a first side of the segmented bone;

a second bone-pin clamp positioned on the second arm for securing at least one bone-pin to a second side of the segmented bone;

means for independently and angularly adjusting the first arm relative to the second arm comprising a first gear and a means for rotating the first gear; and means for independently and angularly adjusting the second arm relative to the first arm comprising a second gear and a means for rotating the second gear, wherein at least one bone-pin clamp comprises an angular-adjustment assembly to angularly adjust the at least one bone-pin relative to the bone-pin clamp.

67. The device according to claim 66, wherein the angular-adjustment assembly comprises two pin-clamp plates adapted to hold bone-pins between them and an angular-adjustment screw with machine threads, wherein the two pin-clamp plates have "V-shaped" teeth formed in at least a portion of their perimeter which mesh with the machine threads of the angular-adjustment screw, such that rotating the angular-adjustment screw angularly adjusts the two pin-clamp plates.

68. The device according to claim 67, wherein the first pin-clamp plate has a semicircular groove formed therein adapted and configured to receive a bone-pin and the second pin-clamp plate has a "V-shaped" groove formed therein adapted and configured to receive a bone-pin, the pin-clamp plates positioned so that the semi-circular and "V-shaped" grooves oppose each other in order to retain at least one the bone-pins.

69. The device according to claim 66, wherein the first arm is angularly adjustable in a range of about 0° to about 120°.

70. The device according to claim 69, wherein the second arm is angularly adjustable in a range of about 0° to about 120°.

* * * * *